United States Patent
Grüning et al.

[11] Patent Number: 5,837,831
[45] Date of Patent: Nov. 17, 1998

[54] METHOD FOR SEPARATING ALKYL GLYCOSIDES

[75] Inventors: Burghard Grüning, Essen; Siegfried Peter, Uttenreuth-Weiher; Eckhard Weidner, Erlangen; Zhengfeng Zhang, Tutzing, all of Germany

[73] Assignee: Th. Goldschmidt AG, Essen, Germany

[21] Appl. No.: 717,950

[22] Filed: Sep. 23, 1996

[30] Foreign Application Priority Data

Sep. 21, 1996 [DE] Germany .......... 195 35 031.6

[51] Int. Cl.$^6$ .................. C07G 3/00; C07H 1/06
[52] U.S. Cl. .......... 536/18.5; 536/124; 536/127
[58] Field of Search .................. 536/18.5, 124, 536/127

[56] References Cited

U.S. PATENT DOCUMENTS 4,968,787  11/1990  Inada et al. .................. 536/18.5
5,266,690  11/1993  McCurry, Jr. et al. .......... 536/124

FOREIGN PATENT DOCUMENTS

| 0526710 | 2/1993 | European Pat. Off. . |
| 3833780 | 4/1990 | Germany . |
| 3932173 | 4/1991 | Germany . |
| 3940827 | 6/1991 | Germany . |
| 4019175 | 1/1992 | Germany . |

*Primary Examiner*—John Kight
*Assistant Examiner*—Everett White
*Attorney, Agent, or Firm*—Anderson, Kill & Olick, P.C.

[57] ABSTRACT

The invention relates to a method for separating alkyl glycoside mixtures or alcohol-containing alkyl glycoside mixtures by extraction, which is characterized in that the extraction is carried out with an extraction agent, which is close to or below the critical point at a reduced temperature ranging from 0.9 to 1.2, and at pressures, which are selected so that the density of the extraction agent is at least 180 kg/m$^3$.

32 Claims, 1 Drawing Sheet

METHOD FOR SEPARATING ALKYL GLYCOSIDES

BACKGROUND OF THE INVENTION

1. Field of the Invention

The invention relates to a method for separating alkyl glycoside mixtures or alcohol-containing alkyl glycoside mixtures by extraction. Pure alkyl monoglycosides or lightly colored alkyl glycoside mixtures, for example, can be obtained as products.

2. Description of the Prior Art

Alkyl glycosides may be obtained by the reaction of reducing sugars with aliphatic alcohols. As sugars, mono-, di- and polysaccharides come into consideration. Examples are sucrose, maltose, galactose and preferably glucose. These are reacted in the presence of an acidic catalyst at elevated temperatures with aliphatic alcohols having a chain length of up to 30 carbon atoms. The German Offenlegungsschrift 38 33 780 is named as an example. Because of the incompatibility of longer chain alcohols and sugars, a two-step transacetalization method has also been developed. In the first step, a shorter chain alcohol, preferably butanol or propylene glycol is reacted with the sugar to form the glycoside, which is then transglycosidated (Seife, Öle, Fette, Wachse, 118, 1992, pages 894 to 904). The mixtures obtained consist of alkyl oligoglycosides with a different number of sugar units and the unreacted aliphatic alcohols, which are usually used in excess. The excess alcohol can subsequently be removed by distillation (German Offenlegungsschrift 39 32 173).

By the reaction and, above all, by the distillation, the reaction mixture is highly stressed thermally, so that by-products of dark color are formed, which adversely affect the quality of the alkyl glycosides. Various methods for bleaching alkyl glycosides have therefore been described. As examples, the EP-A-0 526 710, the German Offenlegungsschrift 40 19 175 and the German Offenlegungsschrift 39 40 827 are named, in which the bleaching is carried out by irradiation, by addition of hydrogen peroxide or by treatment with ozone.

The alkyl glycosides, obtained after removal of the alcohol, represent a mixture of different proportions of mono-, di-, tri- and higher glycosides. The monoglycoside generally forms the main component. The degree of oligomerization can be determined, within certain limits, by the molar ratio of the educts, the alcohol and the sugar. For example, preferably monoglycoside is obtained by a large excess of alcohol, while higher degrees of oligomerization may be obtained by the least possible excess of alcohol. A low degree of oligomerization is, however, achieved in this way at the expense of a low volume yield, while in reactions, which aim for higher degrees of oligomerization, the viscosity of the reaction mixtures can be very high and the danger of forming polysaccharides increases greatly. Moreover, these variations of the method do not make it possible to obtain pure or largely pure oligomers. A separation of the product mixture, either before or after the removal of the alcohol, into the individual components, such as monoglycoside and diglycoside and higher degrees of oligomerization, has not been described previously and was not possible technically. However, it was possible to achieve this with the method of the present invention. Moreover, it was possible to obtain lightly colored alkyl glycosides with this method, without using a bleaching process.

An object of the present invention is a method for separating alkyl glycoside mixtures or alcohol-containing alkyl glycoside mixtures by extraction. The method is characterized in that the extraction is carried out with an extraction agent, which is close to or below the critical point at a reduced temperature ranging from 0.7 to 1.3 and at pressures, which are selected so that the density of the extraction agent is at least 180 kg/m$^3$. The reduced temperature more preferably ranges from 0.9 to 1.2. As products, pure, decolorized alkyl monoglycosides or lightly colored alkyl polyglycosides can be obtained. The alkyl polyglycosides will usually represent mixtures predominantly of monoglycosides, as well as of di-, tri- and tetraglycosides, which may also contain lesser amounts of higher glycosides.

SUMMARY OF THE INVENTION

The reduced temperature $T_r$ is defined as the dimensionless quantity, which is obtained by dividing the measured temperatures (in degrees Kelvin) by the critical temperature $T_c$ (in degrees Kelvin) of the system according to the following formula $$T_r = T/T_c$$

Preferably, carbon dioxide, hydrocarbons with 1 to 10 carbon atoms and ethers with 2 to 8 carbon atoms or mixtures of these are used as extraction agents.

Up to 35% of low molecular weight aliphatic solvents and/or water can be added to the extraction agent as cosolvents. Examples of aliphatic solvents are aliphatic alcohols such as methanol, ethanol, propanol, iso-propanol, ketones, such as acetone, methyl ethyl ketone and acids, such as formic acid and acetic acid. Ethanol is preferred. By these means, the loading of the middle phase of the extraction can be increased.

As starting products for the fractionation, preferably alkyl glycoside mixtures are used, from which the excess alcohol, originating from the synthesis, has previously been removed. By means of the extraction, the alkyl glycoside mixture can be divided into an extract phase, which contains the alkyl glycosides with a low degree of oligomerization, and a refined phase, which contains the alkyl glycosides with a high degree of oligomerization as well as the colored by-products and impurities. The composition of the extract and refined phases can be adjusted by the extraction agent selected and by choosing suitable conditions, such as the temperature and pressure. For example, it is possible for the extract phase, taken off at the head of a countercurrent column, to contain exclusively alkyl monoglycosides as alkyl glycosides and that the higher alkyl glycosides remain in the refined phase.

In another extreme case, the alkyl glycosides can be extracted almost completely into the extract phase, so that essentially only the small proportion of colored by-products and impurities remains behind in the refined phase. By these means, a decolorization of the alkyl glycosides is additionally achieved. Contrary to bleaching, this decolorization is based, however, on a removal of the colored compounds, as a result of which the quality of the alkyl glycosides is improved.

By selecting suitable conditions, it is possible to separate fractions, which lie between these two extreme cases, such as a fraction, which consists predominantly of mono- to triglycosides. Likewise, it is possible, if it is so desired, to divide an alkyl glycoside mixture into several fractions by repeated extraction under different conditions, for example, in an extraction installation consisting of several extraction columns or by repeated extraction on the same column.

These fractions then have different proportions of the respective alkyl glycosides.

In a different embodiment of the inventive method, alcohol-containing alkyl glycoside mixtures are used, which still contain the excess alcohol originating from the synthesis. The alcohol may have 1 to 30 carbon atoms. Usually it will consist of 4 to 22 carbon atoms. If the alkyl glycosides have been synthesized directly from the fatty alcohols and sugars, the alcohol is a fatty alcohol. During the extraction, the alcohol, because of its similar polarity, usually remains predominantly in the monoglycoside-rich phase, from which it can subsequently be removed by distillation or extraction.

By increasing the temperature and/or lowering the pressure, the products in the extraction agent become insoluble. The extracted alkyl glycoside fraction can thus be separated from the extraction agent in a precipitator. The last residues of the extraction agent can be removed completely by spraying, the products being obtained in a finely divided solid form.

Among other things, the method of this invention provides the following advantages:

a) Pure alkyl glycosides can be separated and recovered.
b) Pure, colorless alkyl glycosides, free of alkyl monoglycosides, can be obtained.
c) Alkyl glycosides can be decolorized by removal of the colored by-products and impurities.
d) The extraction can be conducted countercurrently and continuously.
e) The extraction agents can be removed completely at a low temperature.

Alkyl monoglycosides, particularly alkyl monoglucosides, especially those with alkyl groups, which are derived from fatty alcohol with 10 to 14 carbon atoms, are suitable as particularly effective cleansing surfactants, which are used preferably in surfactant mixtures, which are used, for example, as shampoos, dishwashing rinses or household cleaning agent. Alkyl glycosides with a higher degree of oligomerization have better skin-care properties and can be used in cleansing and skin-care cosmetics.

The extraction can be carried out discontinuously or continuously. For economic reasons, the continuous, countercurrent extraction is preferred.

As alkyl glycosides, which are to be separated by the inventive method, particularly compounds of the general formula

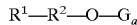

$$R^1-R^2-O-G_a$$

come into consideration. In the above formula, the groups have the following meaning:

$R^1$=a hydrocarbon group with 3 to 21 carbon atoms,
$R^2$=$CH_2$, $(OC_nH_{2n})_m$, in which
  n has an average numerical value of 2 to 4 and preferably of 2 to 3 and
  m has an average numerical value of 1 to 30 and preferably of 1 to 10,
G is a group derived from an aldose or ketose with 5 or 6 carbon atoms, preferably from glucose, and
a has an average numerical value of 1 to 10 and preferably of 1 to 6.

DETAILED DESCRIPTION OF THE PREFERRED EMBODIMENTS

Figure 1:
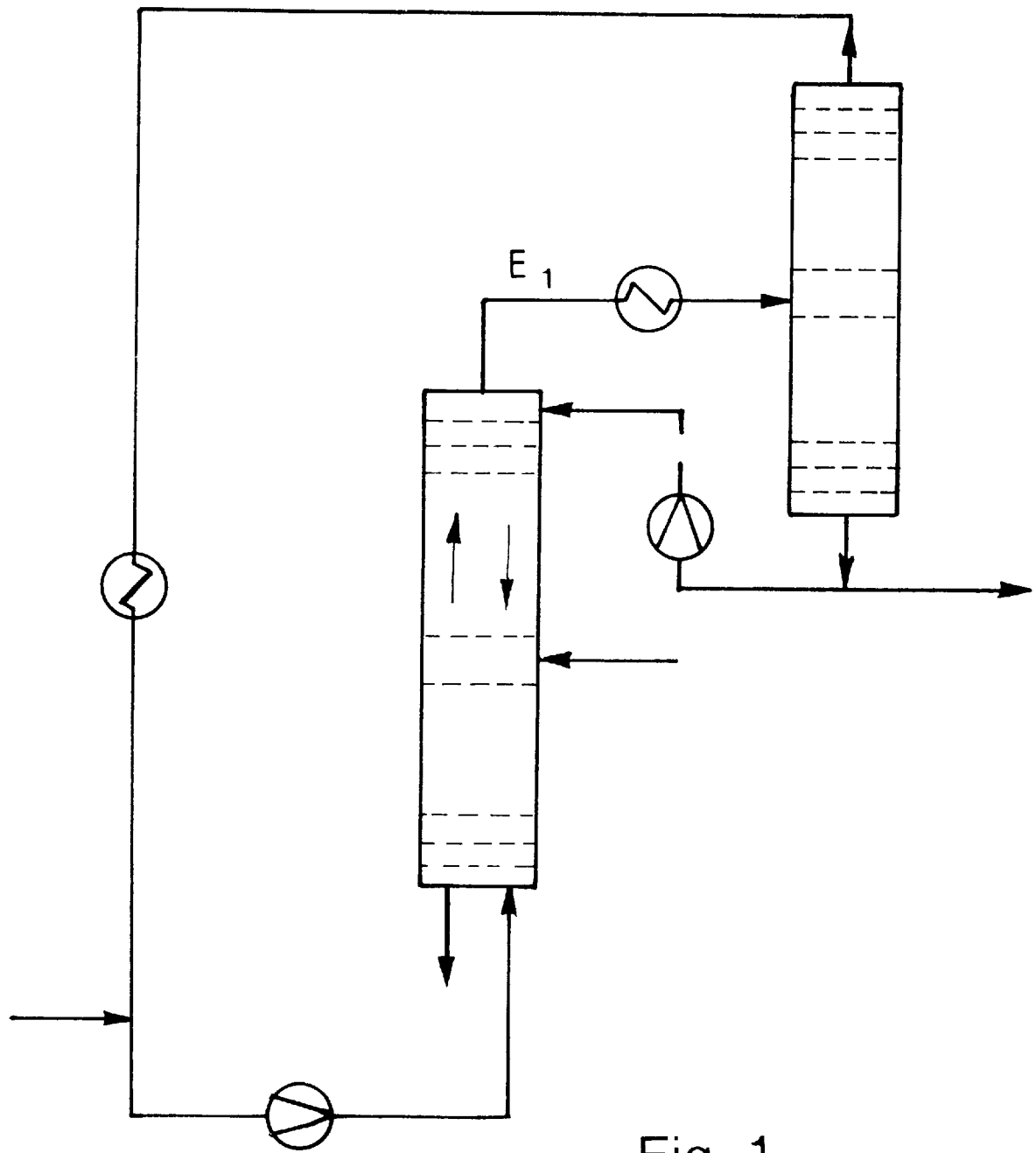
FIG. 1 shows a diagrammatic view of an apparatus for separating alkyl glycoside mixtures or alcohol containing alkyl glycoside mixtures according to the present invention.

By means of the diagrammatic representation of FIG. 1, an embodiment of the inventive method is described in greater detail using alkyl glycosides as an example. The alkylglycoside mixture has previously been separated chiefly from excess free fatty alcohols. The extracted components from the head of the extraction column are separated from the extraction agent in the second column. The apparatus consists of two columns, one of which is the extraction column, the other the regeneration column. The glucoside mixture is supplied to the middle part of the extraction column. The circulating extraction agent, which flows upward in the extraction column, is charged preferably with the more lipophilic components, such as the monoglucosides from the glucoside mixture. The free fatty alcohols also dissolve in the extraction agent. Thus, the monoglucosides are obtained as extract at the head of the column. At the same time, the extraction agent is dissolved in the liquid phase, which is flowing downward and in which the higher molecular weight glycosides are accumlated.

In order to prevent the development of a single phase in the extraction column due to the accumulation of free fatty alcohols, it is advisable, under certain circumstances, to increase the temperature in the direction of the column head. However, this is not required if the original mixture contains small residual amounts (<2%) of free fatty alcohols.

The refined material, which is drawn off at the sump of the extraction column, contains at the extraction pressure enough extraction agent, so that its viscosity is low and blockages of the pipelines and valves do not occur. Advisably, it is sprayed through a nozzle, the pressure dropping to ambient values. At the same time, the extraction agent evaporates and cools the product, so that a solid powder results.

The extraction agent, loaded with the more soluble components, namely the free alcohols and monoglucosides, leaves the booster part of the extraction column (EK) at the head. The pressure on the loaded extraction agent is reduced by means of a pressure-reducing valve to the pressure in the regeneration column. The loaded extraction then passes through a heat exchanger and is supplied to the middle part of the regeneration column. In the regeneration column, the pressure and temperature are selected so that the extraction agent has a density of 150 kg/m³. The regeneration column is operated as a rectifying column. The extraction agent, leaving the head of the regeneration column, is free of dissolved components. The rectification takes place at a pressure, which corresponds to the vapor pressure of the extraction agent at about 25° to 30° C. The vaporous extraction agent is cooled and condensed in a heat exchanger. The liquid extraction agent is pumped back to the extraction column and, before entering the extraction column, heated in a heat exchanger to the extraction temperature. In this way, the expensive recompression of gaseous components is avoided.

At the bottom of the regeneration column, the extract is drawn off. A small portion is pumped back to the extraction column as reflux and the remainder is sprayed through a nozzle, the pressure being reduced to the ambient pressure and remainder of the extraction agent, dissolved in the extract, being evaporated. At the same time, the extract is cooled and obtained in solid form as a powder.

For equipping the columns, packings, which are customary in liquid-liquid extraction and rectifying technology, such as Raschig rings, wire fabric packings, Berlsättel, wire spirals, etc. are, in principle, suitable. The columns may also be equipped with sieve plates.

The method is explained further by means of the following examples. It is understood that the following examples are provided by way of illustration and not by way of any limitation.

EXAMPLE 1

A $C_{12}$–$C_{14}$ alkyl glucoside mixture (250 g), which has the following composition according to analysis (silylation and high-temperature gas chromatography):

| | |
|---|---|
| dodecanol | 1.9% |
| tetradecanol | 3.0% |
| hexadecanol | 0.4% |
| monoglucoside | 70.0% |
| diglucoside | 15.5% |
| triglucoside | 5.3% |
| tetraglucoside | 1.7% |
| pentaglucoside | 0.7% |
| glucose | 1.5% | and 130 g of ethanol are added to an electrically heated 1 L shaking autoclave and heated to 105° C. About 250 g of butane are then pumped in and good mixing, until equilibrium has set in, is ensured by shaking the autoclave. The pressure in the autoclave is about 23 bar. After the autoclave is stopped, a butane-rich (referred to below as gaseous phase) and a liquid phase rapidly separate. (Under the conditions given, butane is below its critical temperature and above its vapor pressure, that is, in the liquid state. Two liquid phases of different composition are therefore formed.) Samples are taken from the two phases with the help of a capillary with an internal diameter of 0.3 mm and analyzed. After the butane and ethanol are evaporated off, the composition of the dissolved, nonvolatile portion of the two phases is determined by high temperature gas chromatography.

Composition of the gaseous phase without the ethanol and butane is as follows:

| | |
|---|---|
| fatty alcohol | 19.2% |
| monoglucoside | 69.9% |
| diglucoside | 7.7% |
| triglucoside | 1.7% |
| tetraglucoside | 1.3% |

Composition of the liquid phase without the ethanol and butane is as follows:

| | |
|---|---|
| fatty alcohol | 2.7% |
| monoglucoside | 68.8% |
| diglucoside | 17.5% |
| triglucoside | 6.5% |
| tetraglucoside | 3.3% |

The monoglucoside/diglucoside separation factor is 2.4. The gaseous phase contains 5.8% of nonvolatile components in solution and the liquid phase 60%. The gaseous phase contains 16% ethanol and 78% butane, while the liquid phase contains 12% ethanol and 28% butane.

EXAMPLE 2

A $C_{12}$–$C_{14}$ alkyl glucoside mixture (250 g), which has the following composition according to analysis (silylation and high-temperature gas chromatography):

| | |
|---|---|
| fatty alcohol | 5.3% |
| monoglucoside | 70.0% |
| diglucoside | 15.5% |
| triglucoside | 5.3% |
| tetraglucoside | 1.7% |
| pentaglucoside | 0.7% |
| glucose | 1.5% | is added to an electrically heated 1 L shaking autoclave and heated to 70° C. About 200 g of dimethyl ether and subsequently carbon dioxide are then pumped in up to a pressure of 70 bar. Under these conditions, the mixture of carbon dioxide and dimethyl ether forms a single phase and acts as a uniform extraction agent. Good mixing is ensured by shaking the autoclave. After the autoclave is stopped, a gaseous phase and a liquid phase rapidly separate. Samples are taken from the two phases with the help of a capillary with an internal diameter of 0.3 mm and analyzed. After the carbon dioxide and the dimethyl ether are evaporated off, the composition of the nonvolatile portion of the two phases is determined by high temperature gas chromatography. The loading of the gas phase is 3.2%.

The composition of the gaseous phase after removal of the carbon dioxide and dimethyl ether is as follows:

| | |
|---|---|
| fatty alcohol | 39.4% |
| monoglucoside | 54.4% |
| diglucoside | 3.6% |
| triglucoside | 0.3% |

The composition of the liquid phase without the carbon dioxide and the dimethyl ether is as follows:

| | |
|---|---|
| fatty alcohol | 2.9% |
| monoglucoside | 71.1% |
| diglucoside | 15.7% |
| triglucoside | 5.0% |
| tetraglucoside | 3.5% |
| pentaglucoside | 0.5% |
| glucose | 1.8% |

The mixture of extraction agents in the gaseous phase consists of 25% carbon dioxide and 75% dimethyl ether. The liquid phase contains 30% dimethyl ether and 7% carbon dioxide.

EXAMPLE 3

A $C_{12}$–$C_{14}$ alkyl glucoside mixture (250 g), which has the following composition according to analysis (silylation and high-temperature gas chromatography):

| | |
|---|---|
| fatty alcohol | 3.2% |
| monoglucoside | 71.6% |
| diglucoside | 15.8% |
| triglucoside | 5.4% |
| tetraglucoside | 1.7% |
| pentaglucoside | 0.7% |
| glucose | 1.5% | and 70 g of dimethyl ether are added to an electrically heated 1 L shaking autoclave and heated to 60° C. About 270 g of propane are then pumped in and good mixing, until equilibrium has set in, is ensured by shaking the autoclave. The pressure in the autoclave is about 50 bar. After the autoclave is stopped, a propane-rich (referred to in the following as gaseous phase) and a liquid phase rapidly separate. At the temperature given, the propane is below its critical temperature and its vapor pressure is less than the process pressure. Accordingly, two liquid phases of different composition are present in equilibrium. Samples are taken from the two phases with the help of a capillary with an internal diameter of 0.3 mm and analyzed. After the propane and dimethyl ether are evaporated off, the composition of the nonvolatile portion in the two phases is determined by silylation followed by high temperature gas chromatography. The loading of the gas phase with nonvolatile portions is 7% by weight.

Composition of the gas phase without the ethanol and propane:

| fatty alcohol | 12.5% |
|---|---|
| monoglucoside | 75.4% |
| diglucoside | 8.0% |
| triglucoside | 1.8% |
| tetraglucoside | 1.3% |

Composition of the liquid phase without the dimethyl ether and propane is as follows:

| fatty alcohol | 2.4% |
|---|---|
| monoglucoside | 71.2% |
| diglucoside | 16.5% |
| triglucoside | 5.7% |
| tetraglucoside | 1.7% |
| pentaglucoside | 0.1% |
| glucose | 1.7% |

The monoglucoside/diglucoside separation factor is 2.2. The gaseous phase contains 7% of nonvolatile components in solution and the liquid phase 60%. The gaseous phase contains dimethyl ether and propane in the ratio of 1 to 4, while the liquid phase contains dimethyl ether and propane in the ratio of 45 to 55 in solution.

EXAMPLE 4

A $C_{12}$–$C_{14}$ alkyl glucoside mixture, which has the following composition:

| free fatty alcohols | 5.3% |
|---|---|
| monoglucosides | 70.0% |
| diglucosides | 15.5% |
| triglucosides | 5.3% |
| tetraglucosides | 1.7% |
| pentaglucosides | 0.7% |
| glucose | 1.5% | is mixed in a pressure vessel with 15% dimethyl ether, a pumpable liquid being formed. The liquid phase obtained is pumped into the middle region of an extraction column of an installation of FIG. 1 at a rate of 2 kg/h. On the way from the pump to the column, the temperature of the mixture is adjusted to 60° C. in a heat exchanger. The 4 m high extraction column is filled with a Sulzer CY packing. In the extraction column, the liquid solution of dimethyl ether in the alkyl glycoside is brought into countercurrent contact with an extraction agent, which consists of a mixture of 80% propane and 20% dimethyl ether, at a pressure of 50 bar and a temperature of 60° C. Because of its higher density, the liquid alkyl glucoside mixture flows downward through the column. The extraction agent flows through the column from the bottom to the top. At the same time, monoglucosides and free fatty alcohols go into solution preferentially. The extraction agent leaves the extraction column at the head with a loading of 7% and is supplied to the middle region of the regeneration column.

In the regeneration column, the extraction agent and the extract are separated from one another by rectification. The rectification is carried out at a pressure of 12 bar. The temperature at the sump of the regeneration column is 90° C. The extract, which is drawn off at the sum of the regeneration column, still contains enough dimethyl ether and propane, so that the mixture is present as a liquid. A portion of the extract is returned to the head of the extraction column as reflux. While the pressure on the extract is being lowered to the ambient pressure, the extract is sprayed. At the same time, the dimethyl ether and the propane are evaporated and the extract is obtained as a powder.

At a solvent to feed ratio of 9, 63% of the feed material is obtained as extract of the following composition:

| free fatty alcohols | 8.4% |
|---|---|
| monoglucosides | 86.0% |
| diglucosides | 5.4% |
| triglucosides | 0.1% |

The refined material, which constitutes 37% of the feed material, has the following composition:

| free fatty alcohols | — |
|---|---|
| monoglucosides | 42.7% |
| diglucosides | 32.7% |
| triglucosides | 14.1% |
| tetraglucoside | 4.6% |
| pentaglucosides | 1.9% |
| glucose | 4.1% |

EXAMPLE 5

An alkyl glucoside mixture with a high content of stearyl polyglucosides has the following composition:

| free fatty alcohols | 1.2% |
|---|---|
| monoglucosides | 72.8% |
| diglucosides | 16.2% |
| triglucosides | 5.5% |
| tetraglucoside | 1.8% |
| pentaglucosides | 0.7% |
| glucose | 1.8% |

The mixture is mixed in a pressure vessel with 20% dimethyl ether (referred to in the following as DME) at ambient temperature, a pumpable liquid being formed. The liquid phase obtained is pumped into the middle of an extraction column of an installation like that of FIG. 1 at the rate of 1.0 kg/h. On the way from the pump to the column, the mixture is heated in a heat exchanger to 140° C. The 4 m high extraction column is filled with a Sulzer CY packing. In the extraction column, the liquid mixture of alkyl glucoside and DME is brought countercurrently into contact with DME as extraction agent at a pressure of 60 bar and a temperature of 140° C. Because of its high density, the liquid alkyl glucoside mixture flows downward in the column. The extraction agent flows through the column from the bottom to the top. At the same time, monoglucosides and free fatty alcohols preferentially go into solution. The extraction agent leaves the extraction column at the head with a loading of about 6% and is taken to the middle region of the regeneration column.

In the regeneration column, the extraction agent and the extract are separated from one another by reducing the pressure to 30 bar. At the same time, the temperature drops as a result of taking the extraction agent out of solution. The extract, which is obtained at the sump of the regeneration column still contains sufficient DME in solution to be present in the liquid state. A portion of the extract is returned as reflux to the head of the extraction column. While the pressure on the extract is being lowered to ambient pressure, the extract is sprayed. At the same time, the dissolved dimethyl ether evaporates and the extract is obtained as a powder.

The extraction agent, leaving the regeneration column, is cooled to about 40° C. and condensed. The liquid DME is brought to the extraction pressure, subsequently heated in a heat exchanger to 140° C. and returned to the extraction column.

For a solvent to feed ratio of about 15, 79.8% of the feed material is obtained as extract of the following composition (after deducting the dissolved extraction agent):

| free fatty alcohols | 1.4% |
|---|---|
| monoglucosides | 89.5% |
| diglucosides | 7.3% |
| triglucosides | 1.1% |
| tetraglucosides | 0.4% |

The refined material, which constitutes 20.2% of the feed material, has the following composition (after deducting the extraction agent):

| free fatty alcohols | — |
|---|---|
| monoglucosides | 5.9% |
| diglucosides | 51.5% |
| triglucosides | 22.8% |
| tetraglucosides | 7.4% |
| pentaglucosides | 3.5% |
| glucosides | 8.9% |

EXAMPLE 6

An alkyl glucoside mixture with a high content of stearyl glucosides, has the following composition:

| free fatty alcohols | 74.4% |
|---|---|
| monoglucosides | 20.3% |
| diglucosides | 3.4% |
| triglucosides | 1.1% |
| tetraglucosides | 0.7% |
| pentaglucosides | — |
| glucose | 0.9% |

The mixture is pumped to the middle region of the extraction column of an installation, similar to that of FIG. 1, at the rate of about 1.8 kg/h. On the way from the pump to the column, the alkyl glucoside mixture is heated in a heat exchanger to 120° C. The 4 m high extraction column is filled with a Sulzer CY packing. In the extraction column, the liquid mixture of alkyl glucoside and fatty alcohols is brought countercurrently into contact with a mixture of 90% by weight of propane and 10% by weight of dimethyl ether as extraction agent at a pressure of 70 bar and a temperature of 120° C.

Because of its higher density, the mixture of alkyl glucoside and free fatty alcohols flows through the column from the top to the bottom. The propane flows countercurrently through the column from the bottom to the top. At the same time, the free fatty alcohols and, with them, a portion of the monoglucosides preferentially go into solution. If the extraction is carried out without refluxing, an extract is formed, which may still contain larger proportions of alkyl glucoside and has, for example, the following composition:

| free fatty alcohols | 86.4% |
|---|---|
| monoglucosides | 12.9% |
| diglucosides | 1.0% |
| triglucosides | 0.3% |
| tetraglucosides | 0.1% |
| pentaglucosides | n.d. |

The level of the glucoside content in the extract can be varied by changing the temperature gradient in the extraction column within certain limits.

The refined material, which constitutes 14.1% of the feed material, has the following composition (without the extraction agent).

| free fatty alcohols | 1.6% |
|---|---|
| monoglucosides | 65.2% |
| diglucosides | 17.7% |
| triglucosides | 5.7% |
| tetraglucosides | 4.3% |
| glucose | 6.4% |

In a second extraction step, the free fatty alcohols of the extract are then separated from the glucosides. Propane once again is the extraction agent. The extract of the first step is pumped to the middle region of the extraction column of an installation, similar to that of FIG. 1, at a rate of about 1.8 kg/h. On the way to the column, the extract is heated in a heat exchanger to 120° C. The 4 m high extraction column is filled with a Sulzer CY packing. In the extraction column, the liquid extract is brought countercurrently into contact with propane as extraction agent at a pressure of 70 bar and a temperature of 120° C. The temperature in the extraction column increases from 120° C. at the sump of the column to 140° C. at the head.

Due to the increase in the temperature towards the head of the extraction column, the solubility of the alkyl glucosides in the dense propane is decreased so far, that the losses of alkyl glucosides in conjunction with the discharging of the fatty alcohols are low (less than 3%). At the same time, a portion of the extract is returned as reflux to the head of the extraction column, in order to recover the alkyl glucosides, present in the extract of step 1, completely in the refined material of the second step. The extract of the second step has the following composition:

| free fatty alcohols | 99.5% |
|---|---|
| monoglucosides | 0.4% |
| diglucosides | 0.1% |
| triglucosides | n.d. |
| tetraglucosides | n.d. |

The refined material, which constitutes 14.2% of the feed material has the following composition (without the extraction agent).

| free fatty alcohols | 2.1% |
|---|---|
| monoglucosides | 88.7% |
| diglucosides | 6.3% |
| triglucosides | 2.1% |
| tetraglucosides | 0.7% |

What is claimed as new and desired to be protected by letters patent is set forth in the appended claims.

What is claimed is:

1. A method for separating alkyl glycoside mixtures into fractions of different degrees of polymerization by extraction, with an almost critical or supercritical extraction agent, which is at a reduced temperature ranging from 0.9 to 1.2, and at pressures, wherein the density of the extraction agent is at least 180 kg/m$^3$.

2. The method of claim 1, wherein carbon dioxide, a hydrocarbon having 1 to 10 carbon atoms, or mixture thereof is used as the extraction agent.

3. The method of claim 1, wherein an ether having 2 to 8 carbon atoms is used as the extraction agent.

4. The method of any of claims 1, 2, or 3, wherein dimethyl ether is used as the extraction agent.

5. The method of claim 4, wherein a mixture of dimethyl ether and propane is used as the extraction agent.

6. The method of claim 5, wherein the extraction is carried out at a pressure, which is up to about 80 bar higher than the vapor pressure of the extraction agent over the solution.

7. The method of claim 5, wherein the extraction is carried out countercurrently in several steps.

8. The method of claim 5, wherein the pressure on the extract is relieved through a spray nozzle and the product of said mixture is obtained in the form of a powder.

9. The method of claim 5, wherein the extraction agent is regenerated by rectification at a pressure, which corresponds to the vapor pressure of the extraction agent at 25° to 30° C. or is slightly higher, and the extraction agent is cooled after leaving a regeneration column in a gaseous state, condensed and pumped back in the liquid state into the extraction column.

10. The method of claim 5, wherein low molecular weight, aliphatic solvents, water or both are added in amounts up to about 35% by weight to the extraction agents, which are close to the critical point.

11. The method of claim 5, wherein in a first step of the extraction, the alkyl monoglycoside is extracted completely and the remaining alkyl polyglycosides are separated by a second fractionation into an extract phase with a high concentration of alkyl glycosides and into a phase containing the by-products and impurities.

12. The method of claim 5, wherein an extract phase, with a high content of alkyl glycosides, is separated from impurities which are colored.

13. The method of claim 4, wherein a mixture of dimethyl ether and butane is used as the extraction agent.

14. The method of claim 13, wherein the extraction is carried out at a pressure, which is up to about 80 bar higher than the vapor pressure of the extraction agent over the solution.

15. The method of claim 13, wherein the extraction is carried out countercurrently in several steps.

16. The method of claim 13, wherein the pressure on the extract is relieved through a spray nozzle and the product of said mixture is obtained in the form of a powder.

17. The method of claim 13, wherein the extraction agent is regenerated by rectification at a pressure, which corresponds to the vapor pressure of the extraction agent at 25° to 30° C. or is slightly higher, and the extraction agent is cooled after leaving a regeneration column in a gaseous state, condensed and pumped back in the liquid state into the extraction column.

18. The method of claim 13, wherein low molecular weight, aliphatic solvents, water or both are added in amounts up to about 35% by weight to the extraction agents, which are close to the critical point.

19. The method of claim 13, wherein in a first step of the extraction, the alkyl monoglycoside is extracted completely and the remaining alkyl polyglycosides are separated by a second fractionation into an extract phase with a high concentration of alkyl glycosides and into a phase containing the by-products and impurities.

20. The method of claim 13, wherein an extract phase, with a high content of alkyl glycosides, is separated from impurities which are colored.

21. The method of any of claims 1, 2, or 3, wherein a mixture of dimethyl ether and carbon dioxide is used as the extraction agent.

22. The method of any of claims 1, 2, or 3, wherein ethyl methyl ether is used as the extraction agent.

23. The method of any of claims 1, 2, or 3, wherein propane, butane or a mixture thereof is used as the extraction agent.

24. The method of any of claims 1–3, wherein the extraction is carried out at a pressure, which is up to about 80 bar higher than the vapor pressure of the extraction agent over the solution.

25. The method of claim 24, wherein said pressure is about 10 to 60 bar higher than the vapor pressure of the extraction agent over the solution.

26. The method of any of claims 1–3, wherein the extraction is carried out countercurrently in several steps.

27. The method of any of claims 1–3, wherein the pressure on the extract is relieved through a spray nozzle and the product of said mixture is obtained in the form of a powder.

28. The method of any of claims 1–3, wherein the extraction agent is regenerated by rectification at a pressure, which corresponds to the vapor pressure of the extraction agent at 25° to 30° C. or is slightly higher, and the extraction agent is cooled after leaving a regeneration column in a gaseous state, condensed and pumped back in the liquid state into the extraction column.

29. The method of any of claims 1–3, wherein low molecular weight, aliphatic solvents, water or both are added in amounts up to about 35% by weight to the extraction agents, which are close to the critical point.

30. The method of any of claims 1–3, wherein in a first step of the extraction, the alkyl monoglycoside is extracted completely and the remaining alkyl polyglycosides are separated by a second fractionation into an extract phase with a high concentration of alkyl glycosides and into a phase containing the by-products and impurities.

31. The method of any of claims 1–3, wherein an extract phase, with a high content of alkyl glycosides, is separated from impurities which are colored.

32. The method of claim 31, wherein a first step, an extract phase with a high alkyl glycoside content is separated from colored impurities and alkyl monoglucoside is removed from the extract phase in further extraction steps.

* * * * *